United States Patent [19]

de La Poterie et al.

[11] Patent Number: 5,571,858

[45] Date of Patent: Nov. 5, 1996

[54] COLORLESS OR COLORED AQUEOUS NAIL VARNISH CONTAINING A FILM-FORMING POLYMER IN THE DISPERSED STATE AND A WATER-SOLUBLE PERFLUOROALKYL COMPOUND

[75] Inventors: Valérie de La Poterie, Rungis; Myriam Mellul, L'Hay Les Roses, both of France

[73] Assignee: L'Oreal, Paris, France

[21] Appl. No.: 249,877

[22] Filed: May 25, 1994

[30] Foreign Application Priority Data

May 26, 1993 [FR] France .................. 93 06329

[51] Int. Cl.⁶ .......................................... C08K 5/02
[52] U.S. Cl. .................. 524/462; 524/463; 524/589; 524/590; 524/556; 524/577
[58] Field of Search .................. 524/462, 463, 524/589, 590, 556, 577

[56] References Cited

U.S. PATENT DOCUMENTS 5,264,242  11/1993  Speer ........................ 427/140
5,284,885   2/1994  Nehra ........................ 524/31

FOREIGN PATENT DOCUMENTS

| 0558423 | 9/1993 | European Pat. Off. . |
| 2677982 | 12/1992 | France . |
| 1032367 | 6/1966 | United Kingdom . |
| 1074201 | 6/1967 | United Kingdom . |
| 8806434 | 9/1988 | WIPO . |
| 9311103 | 6/1993 | WIPO . |

*Primary Examiner*—Paul J. Thibodeau
*Assistant Examiner*—Mary Crithard
*Attorney, Agent, or Firm*—Cushman Darby & Cushman, L.L.P.

[57] ABSTRACT

The present invention provides colored and colorless aqueous nail varnishes which contain 10 to 59% by weight of a film forming polymer present in a dispersed state, from 0.01 to 1% by weight of a water-soluble perfluoroalkyl compound and form 40 to 90% by weight of water. The presence of the water-soluble perfluoroalkyl compound makes it possible to provide excellent aqueous nail varnishes with improved spreading properties.

5 Claims, No Drawings

COLORLESS OR COLORED AQUEOUS NAIL VARNISH CONTAINING A FILM-FORMING POLYMER IN THE DISPERSED STATE AND A WATER-SOLUBLE PERFLUOROALKYL COMPOUND

The present invention relates to a cosmetic composition in the form of a colored or colorless aqueous nail varnish containing a film-forming polymer in the dispersed state and at least one water-soluble organic compound of the perfluoroalkyl type.

At the present time most compositions which are in the form of nail varnish are based on a mixture of organic solvents containing nitrocellulose, an arylsulphonamide-formaldehyde resin or an alkyd resin and a plasticizing agent. Because of the presence of organic solvents, such varnishes have a number of disadvantages insofar as they can damage the nails or the cuticle and, furthermore, cause some hazard to the female users during the application and drying.

Research has therefore been aimed for a number of years at the development of nail varnishes free from organic solvents, and in particular of aqueous varnishes.

While some results have been successfully obtained with the aid of such aqueous nail varnishes, it has been found that the presence of a high proportion of water resulted in a mediocre spreading of the varnish on the surface of the nails, reflected especially in the formation of pits or of shrinkage of the varnish.

The problem of the spreading of a varnish is actually crucial for a uniform application and good coating of the nail surface.

This problem is closely related to the surface tension of the nail varnish composition, which must be as low as possible with a view to obtaining good spreading of the varnish on the nail.

It is well known from the state of the art that surface-active agents can lower the surface tension of the aqueous compositions. Nevertheless, it has been found that in the case of aqueous nail varnishes all the surfactants could not contribute this property.

After many investigations, into a large number of surface-active agents, it was found that it was possible to improve the spreading properties of aqueous nail varnishes in particularly significant conditions by employing, as surface-active agents water-soluble organic compounds of the perfluoroalkyl type. The use of such compounds was found, in fact, to be clearly superior to that of surface-active agents especially of the silicone type, which are known to improve spreading.

The use of at least one perfluoroalkyl compound in the aqueous nail varnish compositions has the effect of considerably modifying the spreading characteristics without, however, modifying the intrinsic properties of the varnish.

The subject of the present invention is therefore, as a new industrial product, a colored or color, aqueous nail varnish characterized in that in addition to the usual cosmetic ingredients it contains (a) from 10 to 59% by weight of a film-forming polymer present in the dispersed state, (b) from 0.01 to 1% by weight of a perfluoroalkyl compound in which the alkyl radical has from 3 to 32 carbon atoms, and (c) from 40 to 90% by weight of water, the proportions of (a), (b) and (c) being expressed in relation to the total weight of the varnish, the said perfluoroalkyl compound being chosen from those which have the following formulae (I), (II) and (III):

a) $(C_nF_{2n+1})\text{-}C_2H_4X$   (I)

in which:
the radical $C_nF_{2n+1}$ is linear or branched,
n is between 3 and 16, and
X denotes a radical chosen from:

(i) —$CO_2Y$ (ii) —$SO_3Y$
   Y denoting a hydrogen atom, an alkali metal or an amino group such as an ammonium group, (iii) —$(OC_2H_4)_m$—OH
   m being between 2 and 100, preferably between 4 and 40, (iv) 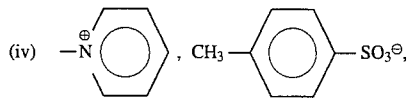

(v) —$SO_2NH(CH_2)_3$—$N^\oplus(CH_3)_3$ $I^\ominus$ (vi) 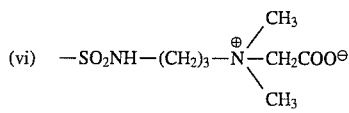

(vii) 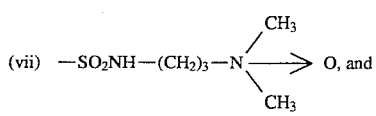

(viii) —$SCH_2CH_2R$
   R denoting either the radical $CO_2M$, M being an alkali metal, in particular lithium, or the radical $N^\oplus(CH_3)_3$ $CH_3SO_4^\ominus$ b) $(C_nF_{2n+1})\text{-}R_1$   (II)

in which:
the radical $C_nF_{2n+1}$ is linear or branched,
n being between 4 and 16, and
$R_1$ is a residue chosen from:
(i) —$SO_3^\ominus NH_4^\oplus$, (ii) —$SO_3^\ominus N^\oplus(R_3)_4$, (iii) —$CO_2^\ominus NH_4^\oplus$, (iv) —$CO_2^\ominus N^\oplus(R_3)_4$,
   $R_3$ being a $C_1$-$C_4$ alkyl radical, (v) —$SO_2N(R_3)CH_2$-$CO_2^\ominus X^\oplus$
   $R_3$ being as defined above, and
   X is a hydrogen atom or an alkali metal, (vi) —$SO_2NH(CH_2)_pN^\oplus(R_3)_3I^\ominus$
   p being 1, 2, 3 or 4, and
   $R_3$ being as defined above, and (vii) —$SO_2N(R_3)(CH_2CH_2O)13$ Y
   Y being a hydrogen atom or a $C_1$-$C_4$ alkyl radical, and
   $R_3$ being as defined above, and c) $(C_nF_{2n+1}C_2H_4O)_xP(O)(R')_y$   (III)

n being between 3 and 8,
x and y, which are different, denote 1 or 2, and
R' denotes $ONH_4$ or OH.

Among the perfluoroalkyl compounds of formula (I) those corresponding to the following formulae may be mentioned in particular:

a) 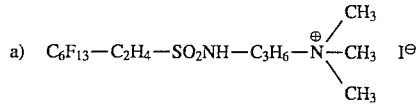

sold under the name of "FORARAC 1179®" by Atochem;

b) 

sold under the name of "FORARAC 1098®" by Atochem;

c) 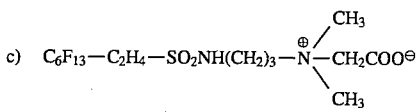

sold under the name of "FORARAC 1157®" by Atochem;

d) $C_nF_{2n+1}CH_2CH_2O(CH_2CH_2O)_xH$
   n=3 to 8 and
   x=2 to 100 sold under the names of "ZONYL-FSN®" and "ZONYL FSN.100®" by Du Pont;

e) $C_nF_{2n+1}CH_2CH_2SCH_2CH_2CO_2Li$
   n=3 to 8 sold under the name of "ZONYL FSA®" by Du Pont;

f) $C_nF_{2n+1}CH_2CH_2SCH_2CH_2N^{\oplus}(CH_3)_3CH_3SO_4^{\ominus}$
   n=3 to 8 sold under the name of "ZONYL FSC®" by Du Pont.

Among the perfluoroalkyl compounds of formula (II) there may be mentioned in particular:

a) $C_nF_{2n+1}SO_2N(C_2H_5)CH_2CO_2^{\ominus}K^{\oplus}$
   n=8 sold under the name of "FLUORAD FC 129®" by 3M;

b) $C_nF_{2n+1}SO_2NHC_3H_6N^{\oplus}(CH_3)_3I^{\ominus}$
   n=8, sold under the name of "FLUORAD FC 135®" by 3M;

c) $C_nF_{2n+1}SO_2N(C_2H_5)(CH_2CH_2O)-H$
   n=8 sold under the name of "FLUORAD FC 170C®" by 3M;

d) $C_nF_{2n+1}SO_3^{\ominus}NH_4^{\oplus}$
   n=10 sold under the name of "FLUORAD FC 120®" by 3M; e) $C_nF_{2n+1}SO_2N(C_2H_5)CH_2CO_2^{\ominus}NH_4^{\oplus}$
   n=8 sold under the name of "FLUORAD FC 143®" by 3M.

Among the perfluoroalkyl compounds of formula (III) there may be mentioned in particular:

a) $(C_nF_{2n+1}CH_2CH_2O)_{1-2}P(O)(ONH_4)_{2-1}$
   n=3 to 8 sold under the name of "ZONYL FSP, FSE®" by Du Pont;

b) $(C_nF_{2n+1}CH_2CH_2O)_{1-2}P(O)(OH)_{2-1}$
   n=3 to 8 sold under the name "ZONYL UR®" by Du Pont,

According to a preferred form of the invention the proportion of the perfluoroalkyl compound is generally between 0.05 and 0.2% by weight relative to the total weight of the nail varnish.

Aqueous dispersions of film-forming polymer are preferably employed for forming nail varnishes according to the invention, Among these dispersions there may be mentioned in particular:

(A) Polyurethane dispersions of anionic, cationic or nonionic type and dispersions of polyurethane copolymers.

Among these dispersions there may be mentioned in particular those described in: Patents EP-143,480 and 391, 322 and in particular those sold by ICI under the names of: "NEOREZ-R974®" and of "NEOPAC-E106®" and by Witco Co. under the name of "WITCOBOND 231®";

(B) Dispersions of acrylic, styrene-based, vinyl and styrene-acrylic polymers and copolymers.

Among these dispersions there may be mentioned in particular those described in: Japanese Patent Applications JP 04-103,511, JP-04-103,512, JP-04-103,513, JP-04-103, 514, JP-04-103,515, JP-04-103,516, JP-54-52,736, JP-55-70,209 and JP-02-221,214, in Patents FR-1,559,020, FR-2, 399,238 and FR-2,537,871, in U.S. Pat. Nos. 4,126,144 and 4,116,913, in Patent EP-140,325, in Patent DE-3,931,237 and in Patent CA-1,225,035, and in particular those sold by ICI under the names of "NEOCRYL-XK53®", "NEOCRYL-XK90®" and "NEOCRYL-XK62®" and by Rhône-Poulenc under the name of "RHODOPASS G5125®".

According to the invention the aqueous nail varnishes may contain various usual cosmetic ingredients and especially organic and inorganic pigments.

Among the organic pigments there may be mentioned: D&C Reds Nos. 10, 11, 12 and 13, D&C Red No. 7, D&C Reds Nos. 5 and 6, D&C Reds Nos. 30 and 34, lacquers such as D&C Yellow No. 5 lacquer and D&C Red No. 2 lacquer. Guanine may also be mentioned.

Among the inorganic pigments there may be mentioned: titaniumdioxide, bismuth oxychloride, brown iron oxide and red iron oxides.

According to this embodiment the pigments are generally present in a proportion of between 0.05 and 5% by weight relative to the total weight of the nail varnish.

Furthermore, some agents such as, for example, clays, hydrated calcium silicate or magnesium silicate may be employed with a view to preventing the pigments from settling.

Among the other ingredients of the nail varnishes according to the invention there may be mentioned preserving agents, perfumes, plasticizers, auxiliary film-forming substances, thickeners, hydrating agents, antifoams, waxes, drying accelerators, UV filters, and a small proportion of other surface-active agents such as those of the silicone type.

A number of examples of aqueous nail varnishes according to the invention will now be given by way of illustration.

In the following examples the letters "AS" mean "Active Substance" that is to say, in this case, the film-forming polymer present, as % in the varnish.

EXAMPLE 1

Colored Nail Varnish

| | |
|---|---|
| Polyurethane dispersion (40% in water) sold by ICI under the name of "NEOREZ-R974 ®" | 70% (28% AS) |
| Pigments | 1.0% |
| Stabilizers | 0.05% |
| Perfluoroalkyl compound sold by Atochem under the name of "FORAFAC 1157 ®" | 0.1% |
| Thickening agent sold by Servo under the name of "SERAD FX 1100 ®" | 0.3% |
| Water q.s. | 100% |

When this varnish is applied onto the nails, the spreading is perfectly uniform and regular. A single application of varnish is sufficient to obtain a regular coat.

After drying, the film obtained is uniform and smooth.

EXAMPLE 2

Colored Nail Varnish

| | |
|---|---|
| Polyurethane dispersion (40% in water) sold by ICI under the name of "NEOREZ R974 ®" | 95% (38% AS) |
| Pigments | 1.5% |
| Perfluoroalkyl compound sold under the name of "FLUORAD FC143 ®" | 0.2% |
| Thickener of the polyurethane type sold by Akzo under the name of "DAPRAL T210 ®" | 0.3% |
| Water q.s. | 100% |

EXAMPLE 3

Colored Nail Varnish

| | |
|---|---|
| Polyurethane dispersion (40% in water) sold by ICI under the name of "NEOREZ R974 ®" | 75% (30% AS) |
| Pigments | 1.5% |
| Perfluoroalkyl compound sold by Du Pont under the name of "ZONYL FSP ®" | 0.2% |
| Thickener of the polyurethane type sold by Akzo under the name of "DAPRAL T210 ®" | 0.4% |
| Water q.s. | 100% |

EXAMPLE 4

Colored Nail Varnish

| | |
|---|---|
| Polyurethane dispersion (40% in water) sold by ICI under the name of "NEOREZ R974 ®" | 70% (28% AS) |
| Pigments | 1.5% |
| Perfluoroalkyl compound sold by Atochem under the name of "FORAFAC 1157 ®" | 0.2% |
| Thickener of the polyurethane type sold by Akzo under the name of "DAPRAL T210 ®" | 0.3% |
| Water q.s. | 100% |

EXAMPLE 5

Colored Nail Varnish

| | |
|---|---|
| Polyurethane dispersion (40% in water) sold by ICI under the name of "NEOREZ R974 ®" | 50% (20% AS) |
| Pigments | 1.5% |
| Perfluoroalkyl compound sold by 3M under the name of "FLUORAD FC143 ®" | 0.1% |
| Thickener of the polyurethane type sold by Akzo under the name "DAPRAL T210 ®" | 0.5% |
| Water q.s. | 100% |

EXAMPLE 6

Colored Nail Varnish

| | |
|---|---|
| Polyurethane dispersion (40% in water) sold by ICI under the name of "NEOREZ R974 ®" | 95% (38% AS) |
| Pigments | 1.5% |
| Perfluoroalkyl compound sold by Atochem under the name of "FORAFAC 1157 ®" | 0.1% |
| Thickener of the polyurethane type sold by Akzo under the name of "DAPRAL T212 ®" | 0.3% |
| Water q.s. | 100% |

EXAMPLE 7

Colored Nail Varnish

| | |
|---|---|
| Polyurethane dispersion (30% in water) sold by Witco under the name of "WITCOBOND 231 ®" | 90% (27% AS) |
| Pigments | 1.5% |
| Perfluoroalkyl compound sold by Atochem under the name of "FLUORAD FC143 ®" | 0.2% |
| Thickener of the polyurethane type sold by Akzo under the name "DAPRAL T210 ®" | 0.3% |
| Water q.s. | 100% |

EXAMPLE 8

Colored Nail Varnish

| | |
|---|---|
| Polyacrylic dispersion (45% in water) sold by ICI under the name of "NEOCRYL XK90 ®" | 60% (27% AS) |
| Pigments | 1.5% |
| Perfluoroalkyl compound sold by Atochem under the name of "FLUORAD FC143 ®" | 0.2% |
| Thickener of the polyurethane type sold by Akzo under the name of "DAPRAL T210 ®" | 0.3% |
| Water q.s. | 100% |

COMPARATIVE EXAMPLES OF NAIL VARNISHES

Example A

| | |
|---|---|
| Polyurethane dispersion (40% in water) sold by ICI under the name of "NEOREZ R974 ®" | 95% (38% AS) |
| Pigments | 1.5% |
| Thickener of the polyurethane type sold by Akzo under the name of "DAPRAL T210 ®" | 0.3% |
| Water q.s. | 100% |

Example B

| | |
|---|---|
| Polyurethane dispersion (40% in water) sold by ICI under the name of "NEOREZ R974 ®" | 95% (38% AS) |

-continued

| | |
|---|---|
| Pigments | 1.5% |
| Silicone surfactant sold by Shin Etsu under the name of "KF 355A ®" | 0.2% |
| Thickener of the polyurethane type sold by Akzo under the name of "DAPRAL T210 ®" | 0.3% |
| Water q.s. | 100% |

Example C

| | |
|---|---|
| Polyurethane dispersion (40% in water) sold by ICI under the name of "NEOREZ R974 ®" | 95% (38% AS) |
| Pigments | 1.5% |
| Silicone surfactant sold by Shin Etsu under the name of "KF 355A ®" | 0.1% |
| Thickener of the polyurethane type sold by Akzo under the name of "DAPRAL T210 ®" | 0.3% |
| Water q.s. | 100% |

The varnishes of Examples 2 to 6 spread regularly and uniformly. A single application of varnish suffices to obtain a regular coat and a smooth film.

The varnishes of Comparative Examples A to C, which do not contain any perfluoroalkyl compound or which contain a silicone compound instead, do not spread uniformly and regularly. The film is not homogeneous and the varnish must be applied several times to obtain a regular coat.

We claim:

1. In an aqueous nail varnish consisting essentially of
   (a) from 10 to 59 percent by weight of a film-forming polymer present in the dispersed state,
   (b) from 0.01 to 1 percent by weight of a water-soluble spreading agent, and
   (c) from 40 to 90 percent by weight of water,
the proportions of (a), (b) and (c) being expressed relative to the total weight of said nail varnish, the improvement comprising, as spreading agent, a perfluoroalkyl compound selected from the group consisting of:

(a) $(C_nF_{2n+1})$-$C_2H_4X$ wherein
the radical $C_nF_{2n+1}$ is linear or branched, n ranges from 4 to 16 and X is a radical selected from the group consisting of:
   (i) —$CO_2Y$
      wherein Y represents hydrogen, an alkali metal or an ammonium group,
   (ii) —$SO_3Y$
      wherein Y represents hydrogen, an alkali metal or an ammonium group,
   (iii) —$(OC_2H_4)_m$-$OH$
      wherein m represents 2 to 100, (iv) 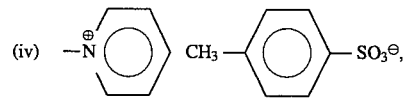

(v) —$SO_2NH(CH_2)_3$—$N^\oplus(CH_3)_3$ $I^\ominus$, (vi) 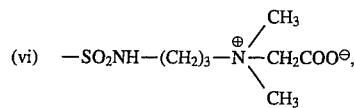

(vii) 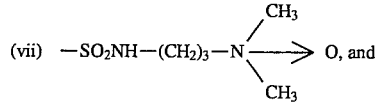

(viii) —$SCH_2CH_2R$
      wherein R represents $CO_2M$, wherein M represents an alkali metal or the radical $N^\oplus(CH_3)_3CH_3SO_4^\ominus$, and (b) $(C_nF_{2n+1}C_2H_4O)_xP(O)(R')_y$ wherein n ranges from 3 to 8
and x and y, which are different, represent 1 or 2 and R' represents $ONH_4$ or OH.

2. The nail varnish of claim 1 wherein said film-forming polymer is selected from the group consisting of an anionic polyurethane, a cationic polyurethane, a nonionic polyurethane, a polyurethane copolymer, an acrylic polymer, an acrylic copolymer, a styrenic polymer, a styrenic copolymer, a vinylic polymer, a vinylic copolymer, a styrenic-acrylic polymer and a styrenic-acrylic copolymer.

3. The nail varnish of claim 1 wherein said water-soluble perfluoroalkyl compound is present in an amount ranging from 0.05 to 0.2 percent by weight relative to the total weight of said nail varnish.

4. The nail varnish of claim 1 further containing at least one organic or inorganic pigment in an amount ranging from 0.05 to 5 percent by weight relative to the total weight of said nail varnish.

5. The nail varnish of claim 1 further containing a nail varnish ingredient selected from the group consisting of an agent preventing pigment settling, a preserving agent, a perfume, a plasticizer, an auxiliary film-forming substance, a thickener, a hydrating agent, an antifoam agent, a wax, a drying accelerator, a UV filter, a silicone type surface-active agent and a mixture thereof.

* * * * *

UNITED STATES PATENT AND TRADEMARK OFFICE
CERTIFICATE OF CORRECTION

PATENT NO. : 5,571,858
DATED : November 5, 1996
INVENTOR(S) : de la Poterie, et al It is certified that error appears in the above-indentified patent and that said Letters Patent is hereby corrected as shown below:

On the title page, item [21] Appl. No.: should read -- 248,877 --.

Signed and Sealed this

Fourth Day of February, 1997

Attest:

BRUCE LEHMAN

*Attesting Officer*            *Commissioner of Patents and Trademarks*